(12) United States Patent
Bhuvanagiri et al.

(10) Patent No.: US 12,105,788 B2
(45) Date of Patent: Oct. 1, 2024

(54) SINGLE SIGN-ON ACROSS MULTIPLE APPLICATION INSTANCES, SUCH AS ELECTRONIC MEDICAL RECORD SYSTEM INSTANCES

(71) Applicant: Providence St. Joseph Health, Seattle, WA (US)

(72) Inventors: Shivudu Bhuvanagiri, Seattle, WA (US); Soumya Sanyal, Seattle, WA (US); Christopher J. Hasz, Seattle, WA (US); Neil W. Black, Seattle, WA (US); Aaron Martin, Seattle, WA (US); Sebastian Jayaraj, Seattle, WA (US)

(73) Assignee: Praia Health Inc., Chicago, IL (US)

( * ) Notice: Subject to any disclaimer, the term of this patent is extended or adjusted under 35 U.S.C. 154(b) by 233 days.

(21) Appl. No.: 17/589,084

(22) Filed: Jan. 31, 2022

(65) Prior Publication Data
US 2023/0205862 A1    Jun. 29, 2023

Related U.S. Application Data

(60) Provisional application No. 63/293,969, filed on Dec. 27, 2021.

(51) Int. Cl.
*H04L 9/40* (2022.01)
*G06F 21/41* (2013.01)
*G16H 10/60* (2018.01)

(52) U.S. Cl.
CPC ........... *G06F 21/41* (2013.01); *G16H 10/60* (2018.01); *H04L 63/0815* (2013.01); *H04L 63/083* (2013.01)

(58) Field of Classification Search
CPC ... G06F 21/41; H04L 63/0815; H04L 63/083; G16H 10/60
See application file for complete search history.

(56) References Cited

U.S. PATENT DOCUMENTS

| | | | |
|---|---|---|---|
| 7,039,656 B1* | 5/2006 | Tsai | G06F 21/31 |
| 7,330,971 B1* | 2/2008 | Kukreja | H04L 63/20 |
| | | | 713/168 |
| 7,428,750 B1* | 9/2008 | Dunn | G06F 21/41 |
| | | | 726/8 |
| 8,201,217 B1* | 6/2012 | Begen | H04L 63/0815 |
| | | | 726/2 |
| 10,353,581 B1 | 7/2019 | Reicher et al. | |

(Continued)

OTHER PUBLICATIONS

Bhuvanagiri, et al., "Single Signon Across Multiple Application Instances, Such as Electronic Medical Record System Instances," U.S. Appl. No. 63/293,969, filed Dec. 27, 2021. (35 pages).

(Continued)

*Primary Examiner* — Viet D Vu
(74) *Attorney, Agent, or Firm* — Seed Intellectual Property Law Group LLP (57) ABSTRACT

A single sign-on facility providing access across multiple application instances is described. The facility receives sign-in data from a user that includes a sign-in name and password. The facility generates a modified sign-in name by adding information identifying a particular application instance to the received sign-in name. The facility then acts on behalf of the user based upon the generated modified sign-in name and the received password.

16 Claims, 12 Drawing Sheets

(56) References Cited

U.S. PATENT DOCUMENTS

| | | | |
|---|---|---|---|
| 2004/0123151 A1* | 6/2004 | Mizrah | H04L 63/102 |
| | | | 726/5 |
| 2008/0167892 A1* | 7/2008 | Clark | G06Q 30/06 |
| | | | 705/1.1 |
| 2012/0291114 A1* | 11/2012 | Poliashenko | G06F 21/41 |
| | | | 726/8 |
| 2013/0166918 A1* | 6/2013 | Shahbazi | H04L 9/0863 |
| | | | 713/183 |
| 2014/0068255 A1 | 3/2014 | Park et al. | |
| 2015/0220746 A1 | 8/2015 | Li et al. | |
| 2015/0379203 A1 | 12/2015 | Douglass | |
| 2017/0124261 A1 | 5/2017 | Mari | |

OTHER PUBLICATIONS

International Search Report and Written Opinion of the International Searching Authority, mailed Mar. 13, 2024, International Application No. PCT/US2023/079779, filed Nov. 15, 2023. (4 pages).

Soohoo et al., "Accessing Patient Electronic Health Record Safety Portals Safely Using Social Credentials: Demonstration Pilot Study", *JMIR Formative Research* 6(1), Jan. 27, 2022. (12 pages).

* cited by examiner

*FIG. 3B* authentication table 400

| Authentication ID | Expanded Sign-In Name | Email Address | Password Hash |
|---|---|---|---|
| 30f0af | psjh.mychart.provorca.alsmith | albertsmith@gmail.com | ... |
| a77523 | psjh.mychart.provak.alsmith | alvin.smith@mailinator.com | ... |
| fd4865 | psjh.mychart.provwamt.alsmith | alsmith@yahoo.com | ... |
| 0b6023 | bshivudu@outlook.com | bshivudu@outlook.com | ... |
| fe201f | neilblum@pobox.com | neilblum@pobox.com | ... |
| c203d1 | plumbernancy@gmail.com | plumbernancy@gmail.com | ... |
| 481820 | spindrift@yahoo.com | spindrift@yahoo.com | ... |

| external identifier table 500 | |
|---|---|
| external system | external identifier type |
| azureB2C | azureB2C |
| auth0 | authID |
| epic | EPI |
| epic | mychartID |
| hpa | hpaID |

511 → external system column; 512 → external identifier type column; 501–505 label the rows.

FIG. 5 external identifier mapping table 600

| Facility Id | External System | External Identifier Type | External Identifier Value |
|---|---|---|---|
| a106 | providence.user.accounts | azureB2C | 30f0af |
| a106 | org.providence.epic.provorca | EPI | E3444 |
| a106 | org.providence.epic.provorca | mychartid | alsmith |
| 9b99 | providence.user.accounts | azureB2C | a77523 |
| 9b99 | org.providence.epic.provak | EPI | E935 |
| 9b99 | org.providence.epic.provak | mychartid | alsmith |
| 8f31 | providence.user.accounts | azureB2C | fd4865 |
| 8f31 | org.providence.epic.provwamt | EPI | E4703 |
| 8f31 | org.providence.epic.provwamt | mychartid | alsmith |
| a8dc | providence.user.accounts | azureB2C | 0b6023 |
| a8dc | org.providence.epic.provak | mychartid | bshivudu |
| a8dc | org.providence.epic.provwamt | mychartid | bshivudu |
| a8dc | org.providence.epic.provwamt | mychartid | bshivudu |
| 0e13 | providence.user.accounts | azureB2C | fe201f |
| 0e13 | org.providence.epic.provorca | mychartid | neilblum |
| 0e13 | org.providence.epic.provwamt | mychartid | neilblum |
| 9160 | providence.user.accounts | azureB2C | c203d1 |
| 9160 | org.providence.epic.provorca | mychartid | doctornancy |
| 9160 | org.providence.hpa.provorcaak | hpaID | nancy.bothanman |
| 7e8c | swedish.user.accounts | authID | 3a897321 |
| 7e8c | org.providence.epic.provwamt | EPI | E9106 |

| external system instance | external system | system type | instance address |
|---|---|---|---|
| providence.user.accounts | azureB2C | authentication | . . . |
| swedish.user.accounts | auth0 | authentication | . . . |
| org.providence.epic.provorca | epic | application | . . . |
| org.providence.epic.provak | epic | application | . . . |
| org.providence.epic.provwamt | epic | application | . . . |
| org.providence.hpa.provorcaak | hpa | application | . . . |
| org.providence.hpa.provwamt | hpa | application | . . . |

FIG. 7

| Facility Id | First Name | Last Name | Preferred Name | Primary Email |
|---|---|---|---|---|
| a106 | Albert | Smith | Al | albertsmith@gmail.com |
| 9b99 | Alvin | Smith | Al | alvin.smith@mailinator.com |
| 8f31 | Albert | Smith | Al | alsmith@yahoo.com |
| a8dc | Shivudu | Bhuvanagiri | Shivudu | bshivudu@outlook.com |
| 0e13 | Neil | Black | Neil | neilblum@pobox.com |
| 910c | Nancy | Bothanman | Nancy | plumbernancy@gmail.com |
| 7e8c | Spindrift | Maxwell | Spin | spindrift@yahoo.com |

*FIG. 12*

SINGLE SIGN-ON ACROSS MULTIPLE APPLICATION INSTANCES, SUCH AS ELECTRONIC MEDICAL RECORD SYSTEM INSTANCES

CROSS-REFERENCE TO RELATED APPLICATION

This application claims the benefit and priority to provisional U.S. Application No. 63/293,969, filed Dec. 27, 2021, the entirety of which is hereby incorporated by reference. In cases where a document incorporated herein by reference conflicts with the present disclosure, the present disclosure controls.

BACKGROUND

Electronic medical records systems ("EMRs," also referred to as electronic health record systems, "EHRs") store, display, and exchange information about patients. The information stored by an EMR about a particular patient is referred to as a record. It is common for EMRs to establish accounts for patients that they can use to view and interact with the information in their records via the web or a smartphone app.

Establishing an account for a patient typically involves creating a sign-in name and password for the patient. Both the sign-in name and the password may be specified either by the EMR or by the patient.

To access his or her record, a patient inputs his or her sign-in name and password into a web form or smartphone app, which forwards them to the EMR. The EMR authenticates the patient, identifies his or her record, and provides access to that record via the patient's web browser or smartphone app.

DETAILED DESCRIPTION

The inventors have recognized that conventional approaches to enabling access to a patient's EMR record by the patient have significant limitations.

In particular, it is common for healthcare systems to operate multiple instances of an EMR. There are a number of scenarios in which this can happen, which include: (1) the EMR limits the amount of information that can be stored in a single instance, or becomes difficult to administer when the information stored in them exceeds a certain size; (2) the healthcare system wants to limit the networking latency, and therefore distance, between patients in a particular geographic area and the server executing those patients' instance; and (3) the healthcare system has grown via consolidation, and it is difficult or impossible to merge the data in instances acquired with different hospitals.

Healthcare systems or other organizations that operate multiple instances of an EMR create a difficult situation for patients: the patient must discover and track in which of the healthcare system's instances the patient has records and take explicit steps to sign into the correct one. Where the patient has records in multiple instances, the patient must often further track different sign-in names and passwords for each of these instances, and coordinate these with the proper instances.

Additionally, where the healthcare system uses additional platforms for other purposes—such as to manage health insurance, access the results of DNA testing or other specialized testing, schedule appointments, conduct video appointments, etc.—each patient typically has separate sign-in names and passwords for these additional platforms, which differ from those the patient has for any EMR instances in which the patient has a record. Some embodiments, the facility permits a patient logged in to the facility to traverse among these different applications to which the patient is registered without reentering any sign-on information.

In response to recognizing these limitations and disadvantages, the inventors have conceived and reduced to practice a software and/or hardware facility that provides a single sign-on across multiple application instances, such as electronic medical record system instances, and/or instances of different applications ("the facility").

For patients that are already enrolled in an EMR instance or an instance of another protected application with a particular sign-in and password, the facility permits the user to authenticate himself or herself to the facility using that sign-in and password, even in cases where another patient is already using that sign-in to authenticate to the facility. In some embodiments, the facility does so by internally expanding each sign-in with additional information about the user, such as the application instance in which the patient has a record. In some embodiments, the facility does so by expanding each sign-in to contain additional details about the corresponding patient that the facility can discern, such as the application instance in which the patient is enrolled. For example, the facility may expand the sign-in ID "alsmith" generated by the patient or an EMR instance in which the patient is enrolled to "psjh.mychart.provorca.alsmith", where "psjh" is the authentication entity, "mychart" is the application, and "provorca" is the instance of the application. In some embodiments, the facility does so by also or instead using passwords to distinguish between two users who use the same sign-in to authenticate to the facility. In some embodiments, the facility uses the same techniques to permit patients to generate their own sign-in for use to authenticate with the facility that is simultaneously being used by another user.

In some embodiments, the facility assigns its own internal identifier to each patient. In various embodiments, this facility identifier is a GUID, or an identifier of another type that is likely to be unique among patients. The facility uses an external identifier mapping table to map between each patient's facility identifier and identifiers assigned to the patient by other systems. In various embodiments these include application instances and user authentication systems.

An authentication system leveraged by the facility maintains an authentication table of patients in which each row corresponds to a different patient, and contains at least the patient's sign-in name, password representation, and the authentication identifier by which the patient is known to the authentication system. The authentication system uses this information to authenticate a user when the facility routes their sign-on request to the authentication system. In some embodiments, the facility supports the simultaneous use of multiple authentication systems, or straightforward migration between them.

By performing in some or all of these ways, the facility enables patients to use pre-existing sign-in information to sign on to the appropriate instance of an EMR or another application, often without having to attend to the identity of the instance or maintain and access separate sign-in information for different applications or application instances to which they are registered.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, offloading interactive authentication from the applications to the facility reduces the processing load on the servers hosting applications; this permits less powerful and less expensive servers—or fewer servers—to be used to host the applications for the same volume of substantive processing by the application, or permits the same number and capability of service to be used for greater volume of substantive processing.

Figure 1:
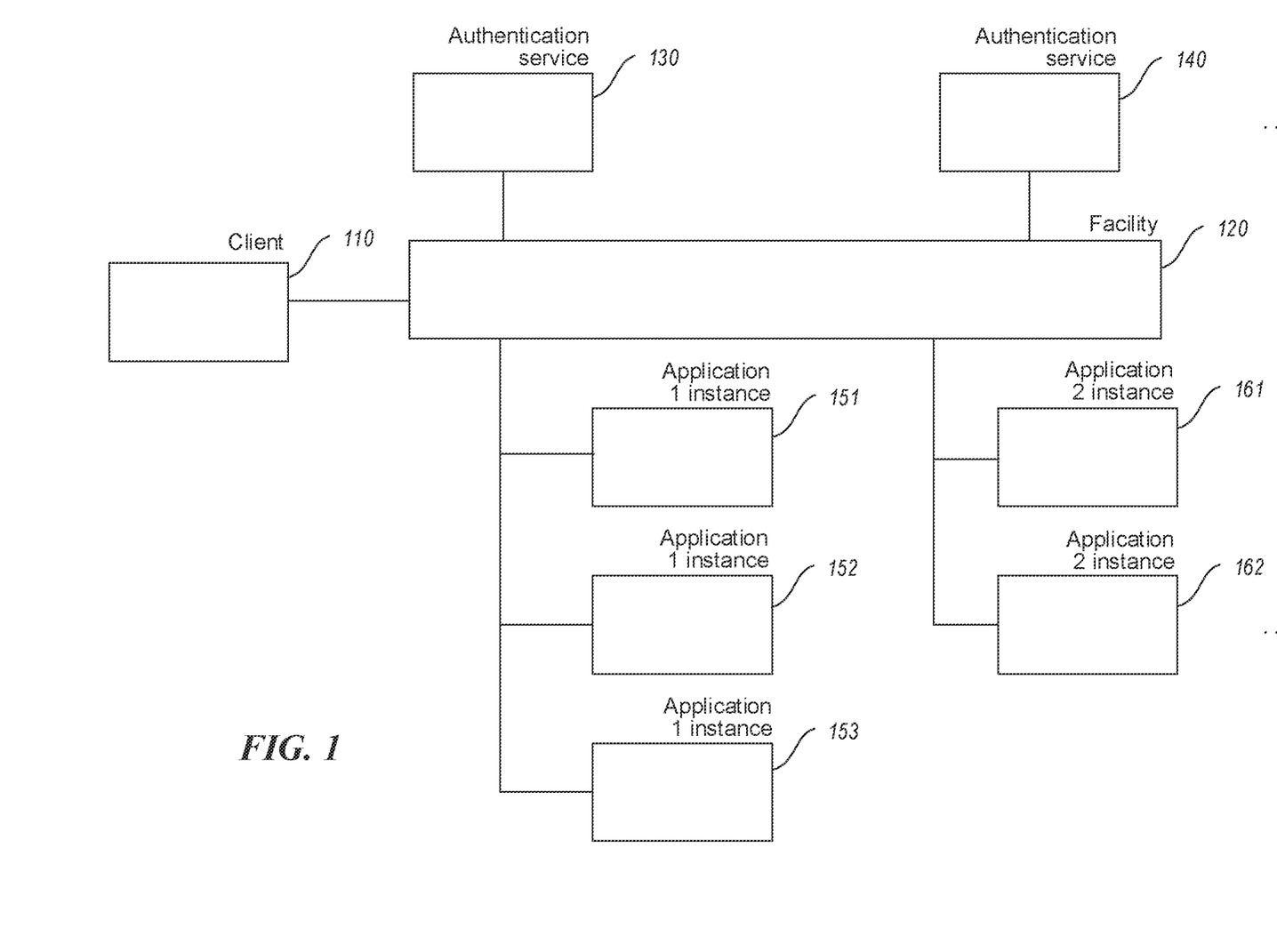
FIG. 1 is a network diagram showing an environment in which the facility operates in some embodiments.

FIG. 1 is a network diagram showing an environment in which the facility operates in some embodiments. The facility 120 executes on one or more servers and is connected by the Internet or another network to a client 110 used by the patient or other user. In various embodiments, the client connects to the facility via a web browser or a smartphone app. In some embodiments, the client's web browser is redirected to the facility by a webpage established for the healthcare system or other authenticating entity, a webpage established for the EMR or other protected application, etc. In some embodiments, the facility forwards or redirects the client to an authentication service such as authentication service 130 or 140. In various embodiments, the authentication service executes on the same server as the facility, or a different server. The authentication system collects sign-on information from the client, such as sign-on name and password. The authentication system uses this information to authenticate the patient against an authentication table described in greater detail below and passes to the facility an authentication ID for the patient contained in the authentication table to indicate the patient's authentication. In various embodiments, the authentication service operates under a variety of levels of control of the facility. In various embodiments, the facility is integrated into the authentication service to various degrees.

In response to authentication by the authentication service, the facility selects among various application instances such as application instances 151, 152, 153, 161, and 162 to automatically authenticate the patient to. The facility uses an external identifier mapping table described in greater detail below to map the authentication identifier received from the authentication system to a facility identifier for the patient, and from that facility identifier to an application identifier for the patient for the selected application instance. The facility calls the selected application instance with the mapped-to application identifier via a secure interface to authenticate the patient to the selected application instance. In some embodiments, after signing into the facility, the patient can specify a different application instance—for the same application or different application—to which they are registered; in response, the facility authenticates the patient to the specified application instance without requiring the patient to provide any additional sign-on information.

In various embodiments, the application instances are instances of an EMR application, such as EPIC from Epic Systems; Praxis EMR from Infor-Med Inc.; Cerner Millenium from Cerner Corporation; and athenaOne from athenahealth, Inc., among others. In various embodiments, the application instances are instances of applications of a wide variety of other types.

Each application protected by the facility uses one or more types of application identifiers to identify its users, which can vary across applications. As one example, for protected instances of the EPIC application, the facility maps from its facility identifier for an authenticated patient to EPI or MRN application identifiers by which the EPIC application identifies its users. Other applications similarly use their own application identifier types.

Figure 2:
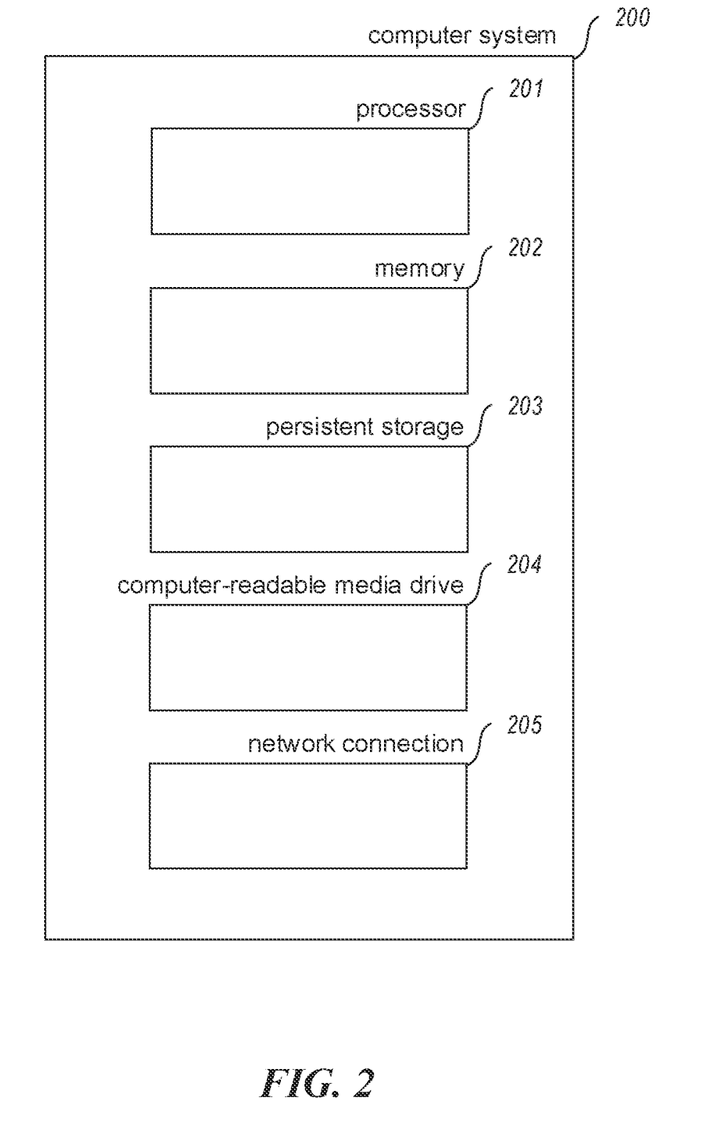
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various embodiments, these computer systems and other devices 200 can include server computer systems, cloud computing platforms or virtual machines in other configurations, desktop computer systems, laptop computer systems, netbooks, mobile phones, personal digital assistants, televisions, cameras, automobile computers, electronic media players, physiological sensing devices, and/or their associated display devices, etc. In various embodiments, the computer systems and devices include zero or more of each of the following: a processor 201 for executing computer programs and/or training or applying machine learning models, such as a CPU, GPU, TPU, NNP, FPGA, or ASIC;

a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations and having various components.

Figure 3A:
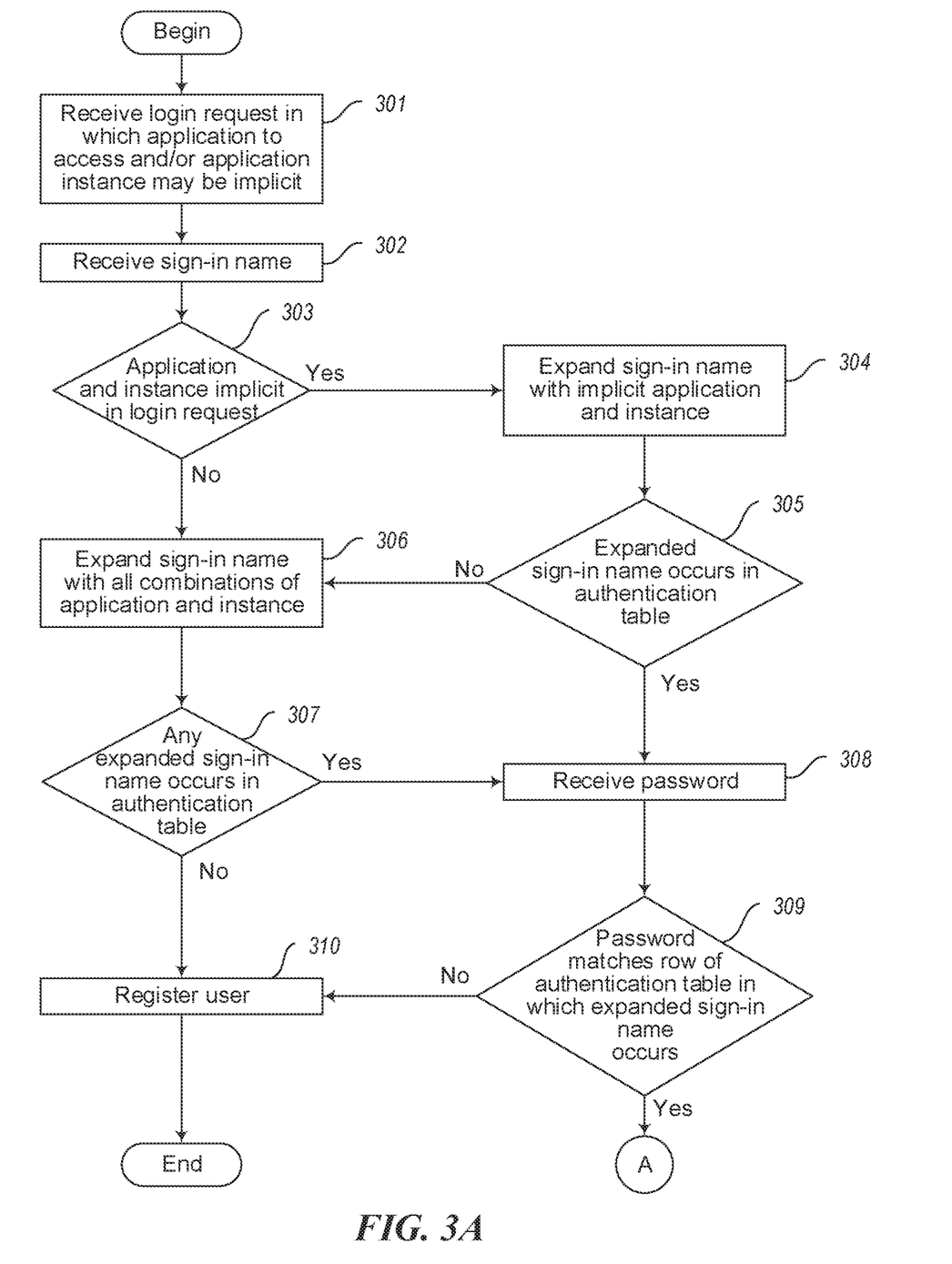
FIGS. 3A-3B show a flow diagram showing a process performed by the facility in some embodiments to sign in a user to the facility and authenticate the user to an application instance.
Figure 3B:
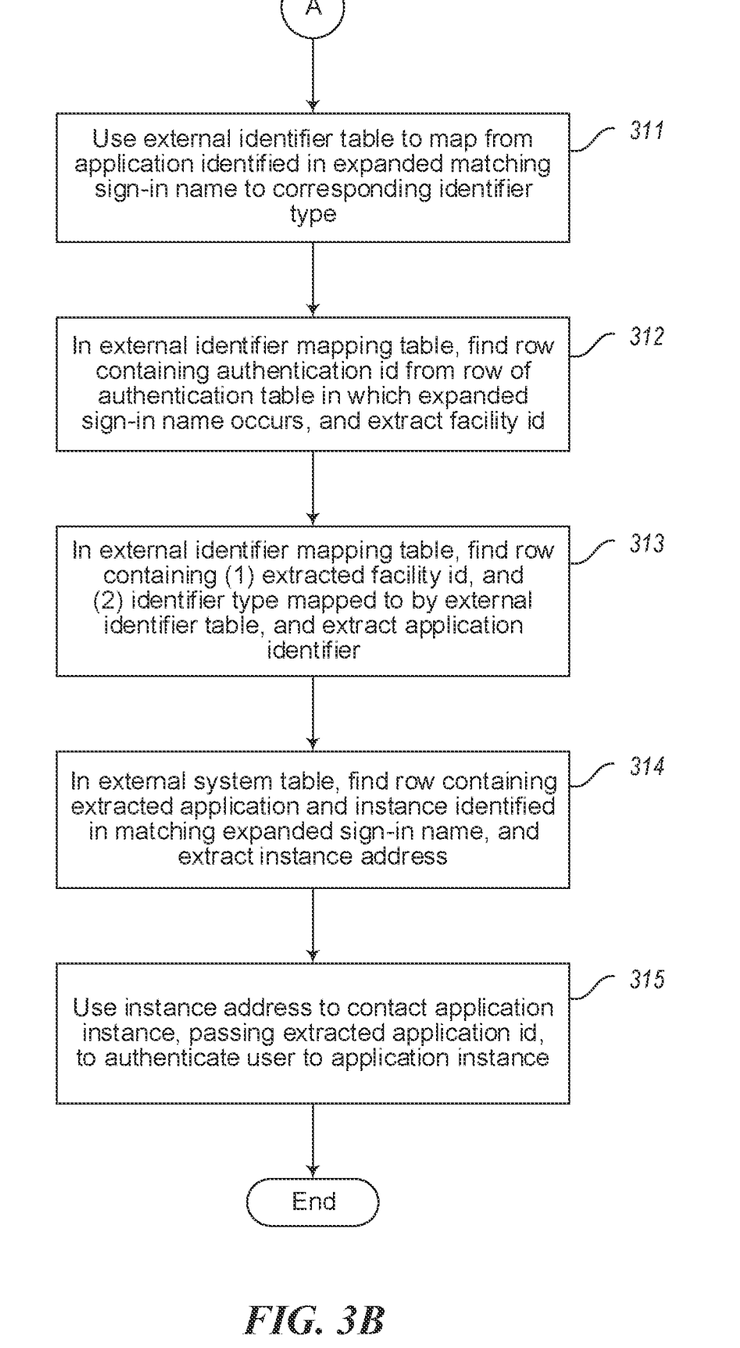

FIGS. 3A-3B show a flow diagram showing a process performed by the facility in some embodiments to sign in a user to the facility and authenticate the user to an application instance. In act 301, the facility receives a login request in which may be implicit a particular application access, and in some cases a particular instance of the application. Where the login request is an HTTP request, in various embodiments this implicit information may be encoded in a referrer header field, in a URL query string argument, etc.

In act 302, the facility receives from the user the user's sign-in name, such as in a posted web form. In act 303, if an application and application instance are implicit in the login request, then the facility continues in act 304, else the facility continues in act 306. In act 304, the facility expands the sign-in name with the application and instance that were implicit in the login request. For example, the facility may expand the sign-in ID "alsmith" to "psjh.mychart.provorca.alsmith", where "psjh" is the authentication entity, "mychart" is the application, and "provorca" is the instance of the application. In act 305, if the expanded sign-in name established by the facility in act 304 occurs in the authentication table maintained by the facility, then the facility continues in act 308, else the facility continues in act 306.

Figure 4:
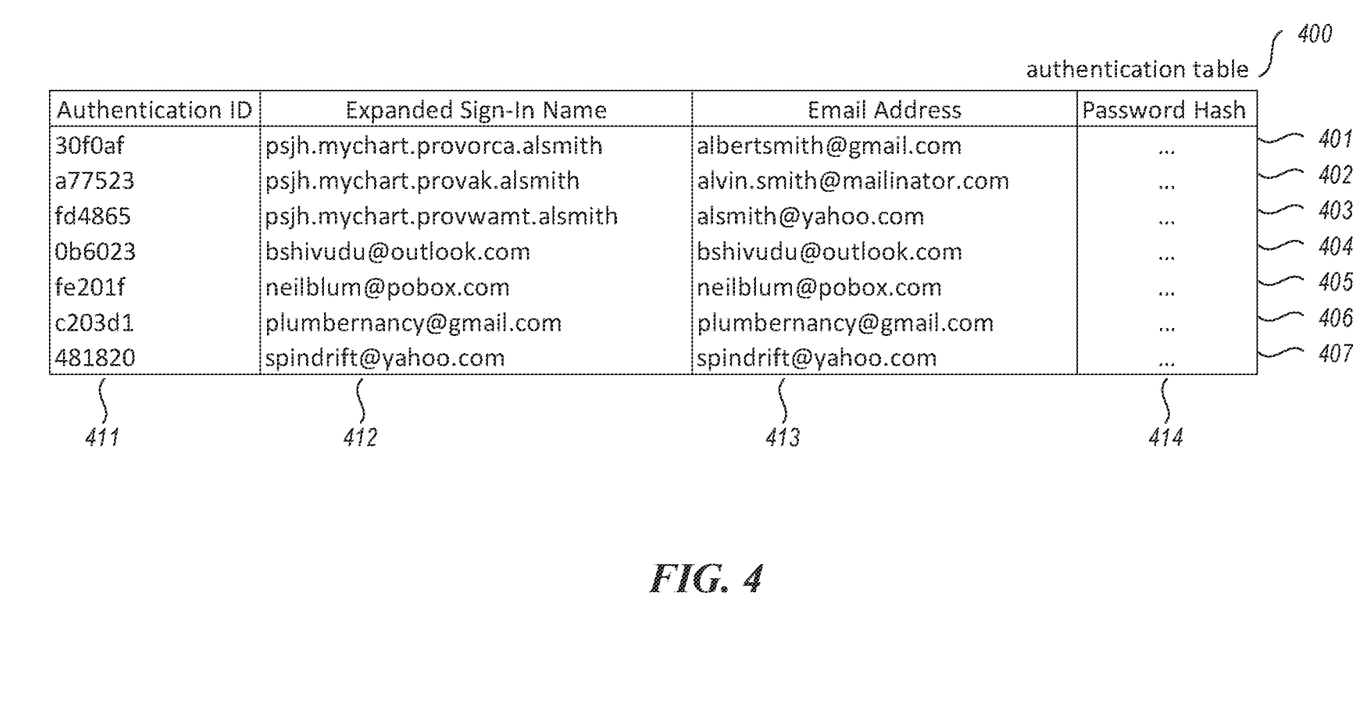
FIG. 4 is a table diagram showing sample contents of an authentication table used by the facility in some embodiments to store information used to authenticate a user to the facility.

FIG. 4 is a table diagram showing sample contents of an authentication table used by the facility in some embodiments to store information used to authenticate a user to the facility. The authentication table 400 is made up of rows such as rows 401-407 each corresponding to a different expanded sign-in name. Each row is divided into the following columns: an expanded sign in name column 412 containing the expanded sign-in name; an authentication ID column 411 containing an identifier assigned to the expanded sign-in name by the authentication system; an email address column 413 containing email address corresponding to the expanded sign-in name; and a password has column 414 containing a hashed version of the password corresponding to the expanded sign-in name. For example, row 401 indicates that the expanded sign-in name "psjh.mychart.provorca.alsmith" as authentication ID "30f0af", email address "albertsmith@gmail.com", and a password hash that is not shown.

While FIG. 4 and each of the table diagrams discussed below show a table whose contents and organization are designed to make them more comprehensible by a human reader, those skilled in the art will appreciate that actual data structures used by the facility to store this information may differ from the table shown, in that they, for example, may be organized in a different manner; may contain more or less information than shown; may be compressed, encrypted, and/or indexed; may contain a much larger number of rows than shown, etc.

Returning to FIG. 3A, in act 306, the facility expands the sign-in name received in act 302 with all combinations of protected applications and their instances. For example, where the sign-in name is "alsmith", the application entity is the Providence Saint Joseph Health healthcare system, the only protected application is mychart, and the three instances of mychart are "provorca", "provak", and "provwamt", the facility expands the sign-in name to "psjh.mychart.provorca.alsmith", "psjh.mychart.provak.alsmith", and "psjh.mychart.provwamt.alsmith".

In act 307, if any of the expanded sign-in names generated by the facility in act 306 occur in the authentication table, then the facility continues in act 308, else the facility continues in act 310. In act 308, the facility receives a password from the user. In act 309, if the password received by the facility in act 308 matches a row of the authentication table in which any of the expanded sign-in names generated in act 304 or 306 occur, then the facility continues through connector A to act 311 in FIG. 3B, else the facility continues in act 310. In act 310, the facility registers the user. The facility's registration of the user is discussed in greater detail below in connection with FIG. 10. After act 310, this process concludes.

In act 311, the facility uses the external identifier table maintained by the facility to map from the application identified in the matching expanded sign-in name to the corresponding external identifier type.

Figure 5:
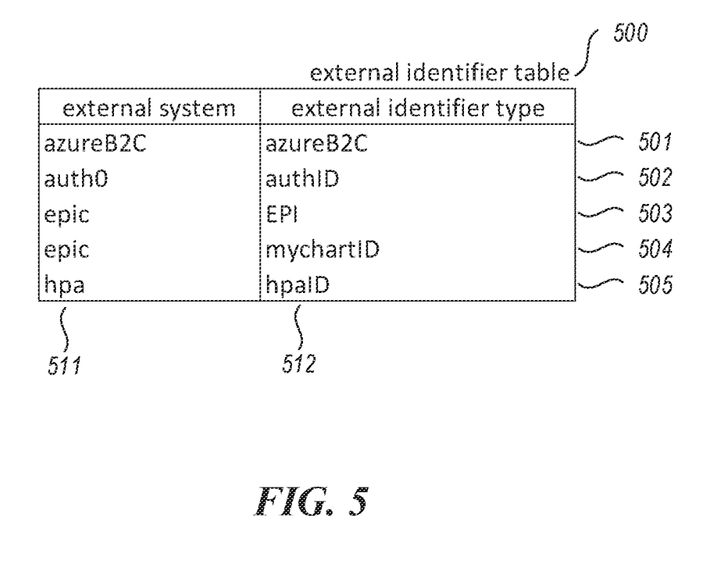
FIG. 5 is a table diagram showing sample contents of an external identifier table used by the facility in some embodiments used by the facility to store associations between external systems and be types of identifiers they used to identify users.

FIG. 5 is a table diagram showing sample contents of an external identifier table used by the facility in some embodiments used by the facility to store associations between external systems and be types of identifiers they used to identify users. The external identifier table 500 is made up of rows such as rows 501-505 each corresponding to a different external system, such as an authentication system or an application. Each row is divided into the following columns: an external system column 511 identifying the external systems, and an external identifier type: 512 containing the type of identifiers used to identify users by the external system. For example, row 503 indicates that the Epic EMR application uses identifiers called EPIs to identify its users.

Returning to FIG. 3B, in act 312, in the external identifier mapping table maintained by the facility, the facility finds a row containing the authentication ID from the row of the authentication table in which expanded sign-in name occurs. From this row, the facility extracts a facility ID.

Figure 6:
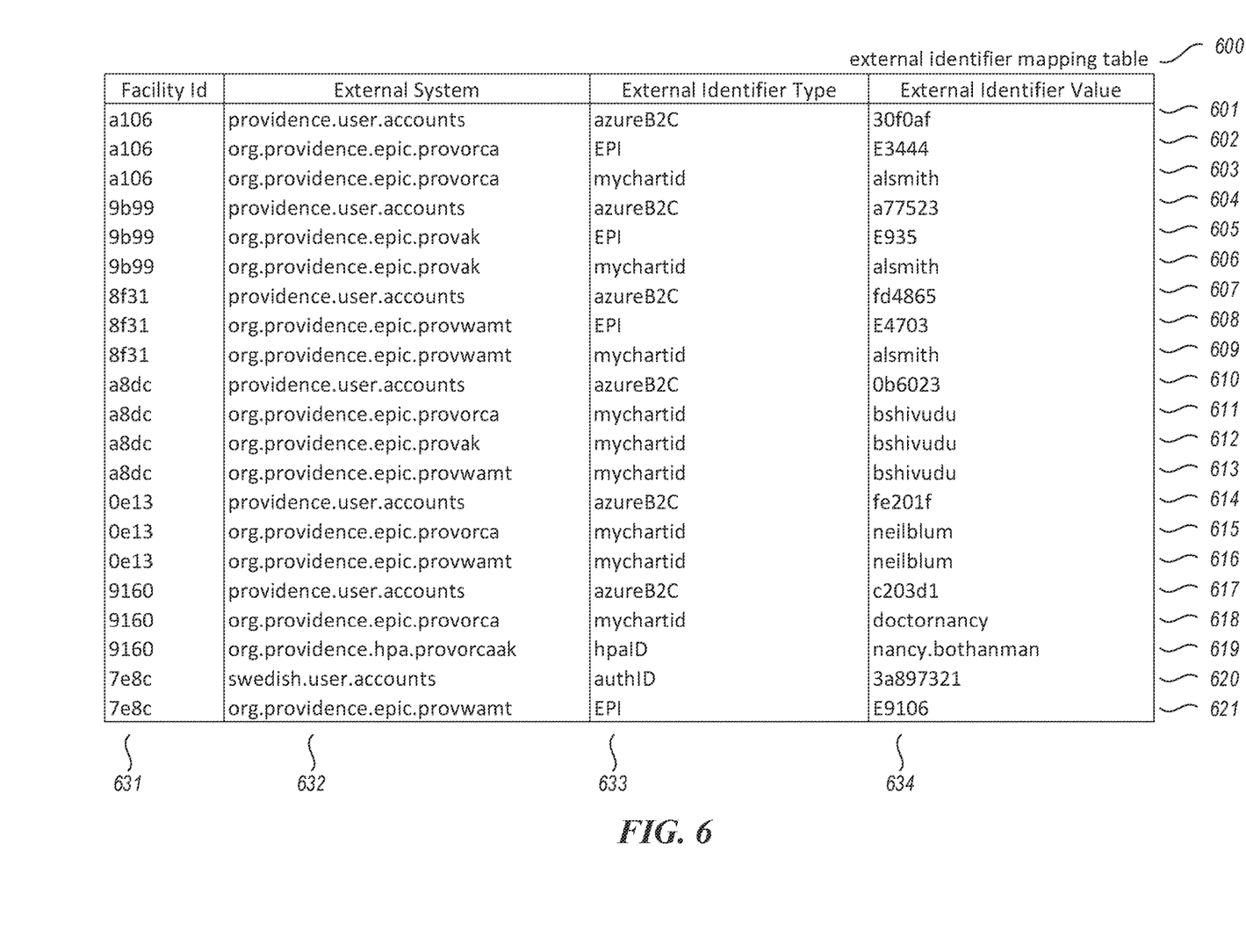
FIG. 6 is a table diagram showing sample contents of an external identifier mapping table used by the facility in some embodiments to store mappings between internal identifiers used by the facility to identify users and identifiers used by authentication systems and application instances to identify the same users.

FIG. 6 is a table diagram showing sample contents of an external identifier mapping table used by the facility in some embodiments to store mappings between internal identifiers used by the facility to identify users and identifiers used by authentication systems and application instances to identify the same users. The table 600 is made up of rows, such as rows 601-621, each corresponding to a different combination of a patient and an external system with which the patient interacts. Each of the rows is divided into the following columns: a facility ID column 631 containing an identifier used by the facility to identify a particular patient; an external system column 632 identifying a system external to the facility that has a different identifier for the user identified by the facility ID; an external identifier type column 633 that identifies the type of the external identifier used by the external system to identify the patient; and an external identifier value column 634 containing the value of the external identifier used by the external system to identify this patient. For example, row 601 indicates that the "providence.user.accounts" external system (an authentication system) uses the identifier"30f0af"—an azureB2C identifier—to identify the patient having facility ID "a106". Thus, where the facility finds that the expanded sign-in name "psjh.mychart.provorca.alsmith" occurs in row 401 of the authentication table, the facility extracts authentication ID "30f0af" from this row of the authentication table; the facility then finds this authentication ID in row 601 of the external identifier mapping table, and extracts from this row of the external identifier mapping table the facility id of "a106" used by the facility to identify this patient.

Returning to FIG. 3B, in act 313, in the external identifier mapping table, the facility finds a row containing both the facility ID extracted in act 312 and the identifier type mapped to by the external identifier table. In the example, the facility ID is "a106", and the identifier type is "EPI". Accordingly, in this example, the facility finds row 602 of the external identifier mapping table, which maps from this facility ID and external identifier type to the external identifier value E344, used by the external system "org.providence.epic.provorca" (an instance of the Epic EMR application) identify this patient.

In act 314, in the external system table maintained by the facility, the facility finds a row containing the application instance identified by the matching expanded sign-in ID, and extracts from it and instance address at which the facility can call the application instance to authenticate a user.

Figure 7:
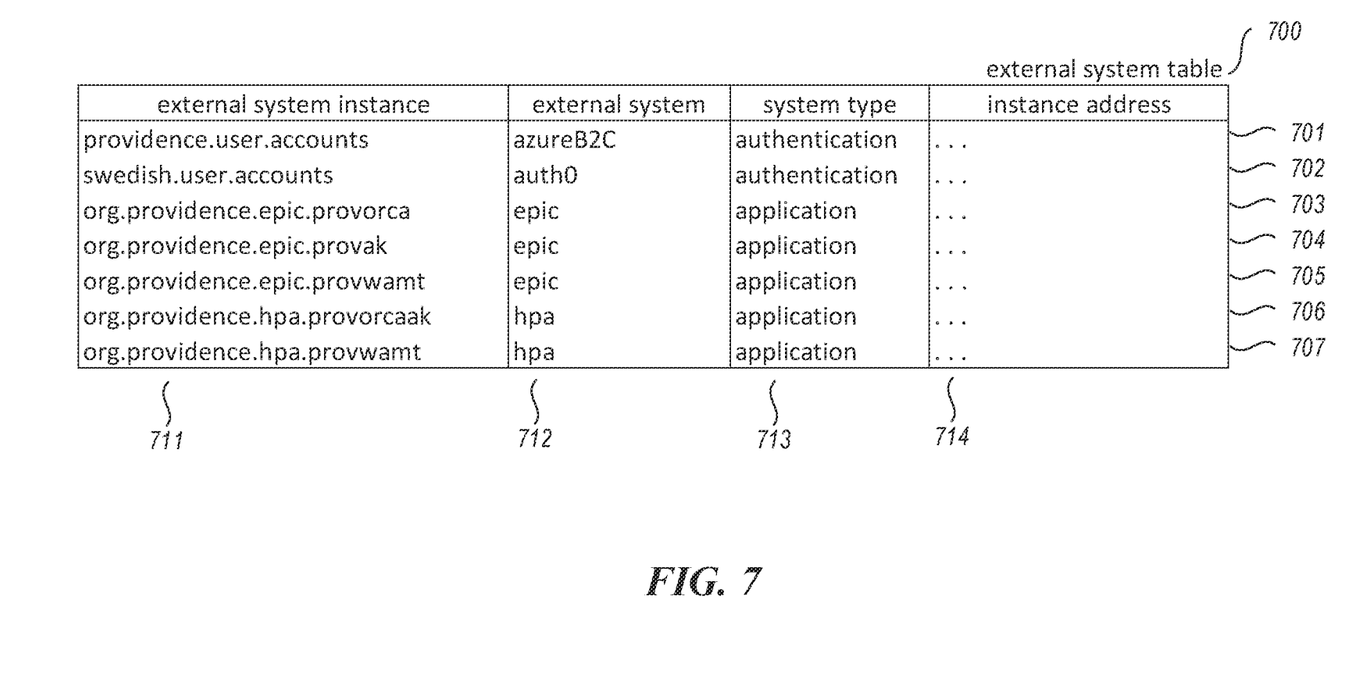
FIG. 7 is a table diagram showing sample contents of an external system table used by the facility in some embodiments to store the mechanism used to call each authorization system and application instance.

FIG. 7 is a table diagram showing sample contents of an external system table used by the facility in some embodiments to store the mechanism used to call each authorization system and application instance. The external system table 700 is made up of rows, such as rows 701-707, each corresponding to a different external system executing an application instance protected by the facility. Each row is divided into the following columns: an external system instance column 711 identifying the application instance to which the row corresponds; and external system column 712 identifying the external system of which the external system instance is an instance; a system type column 713 indicating whether the external system is an authentication system to the an application; and an instance address column 714 specifying a mechanism for the facility to use to call the system instance. For example, row 703 indicates that the external system instance "org.providence.epic.provorca" is an instance of the "epic" external system, which is an application, and contains the address for the facility to use to call that system instance (not shown).

Returning to FIG. 3B, in act 315, the facility uses the instance address extracted from the external system table by the facility in act 314 the contact the application and stamp, passing the application ID extracted in act 313, to authenticate the user to the application instance. At this point, the patient can proceed to use the application instance. In the case of an EMR such as Epic, the user can review their medical record, exchange textual messages with caregivers, request prescription refills, etc. After act 315, this process concludes.

Those skilled in the art will appreciate that the acts shown in FIG. 3 and in each of the flow diagrams discussed below may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

Figure 8:
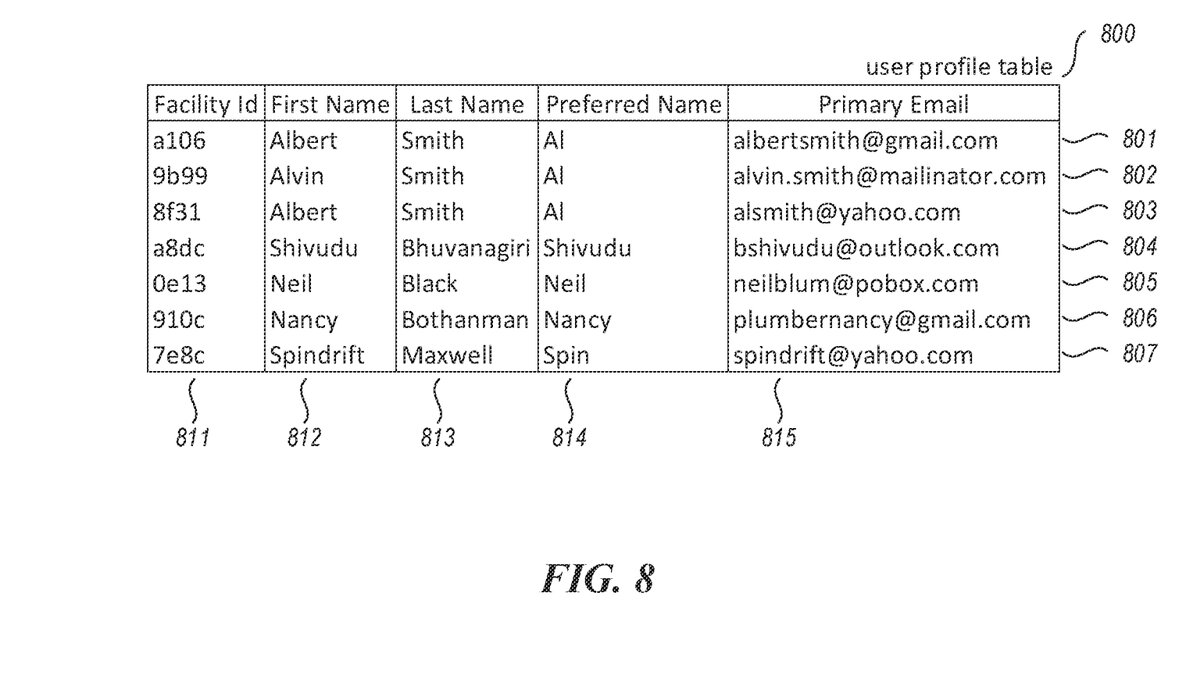
FIG. 8 is a table diagram showing sample contents of a user profile table used by the facility in some embodiments to store user profile information.

In some embodiments, the facility maintains a user profile for patients who are registered with the facility. FIG. 8 is a table diagram showing sample contents of a user profile table used by the facility in some embodiments to store user profile information. The user profile table 800 is made up of rows, such as rows 801-807, that each correspond to a different patient. Each row is divided into the following columns: a facility identifier, 811 containing the identifier by which the facility identifies the patient; first and last name columns 812 and 813 containing the patient's first and last names; a preferred name column 814 containing a version of the patient's first name that the patient prefers to use; and the primary email column 815 containing an email address for the patient. For example, row 801 indicates that the patient having facility ID "a106" has name "Albert Smith", has the preferred name "Al", and the email address "albertsmith@gmail.com". The facility can use this information to interact with the patient; to disambiguate the patient from other patients having the same sign-in name; to interact with external systems about the patient, etc.

Figure 9:
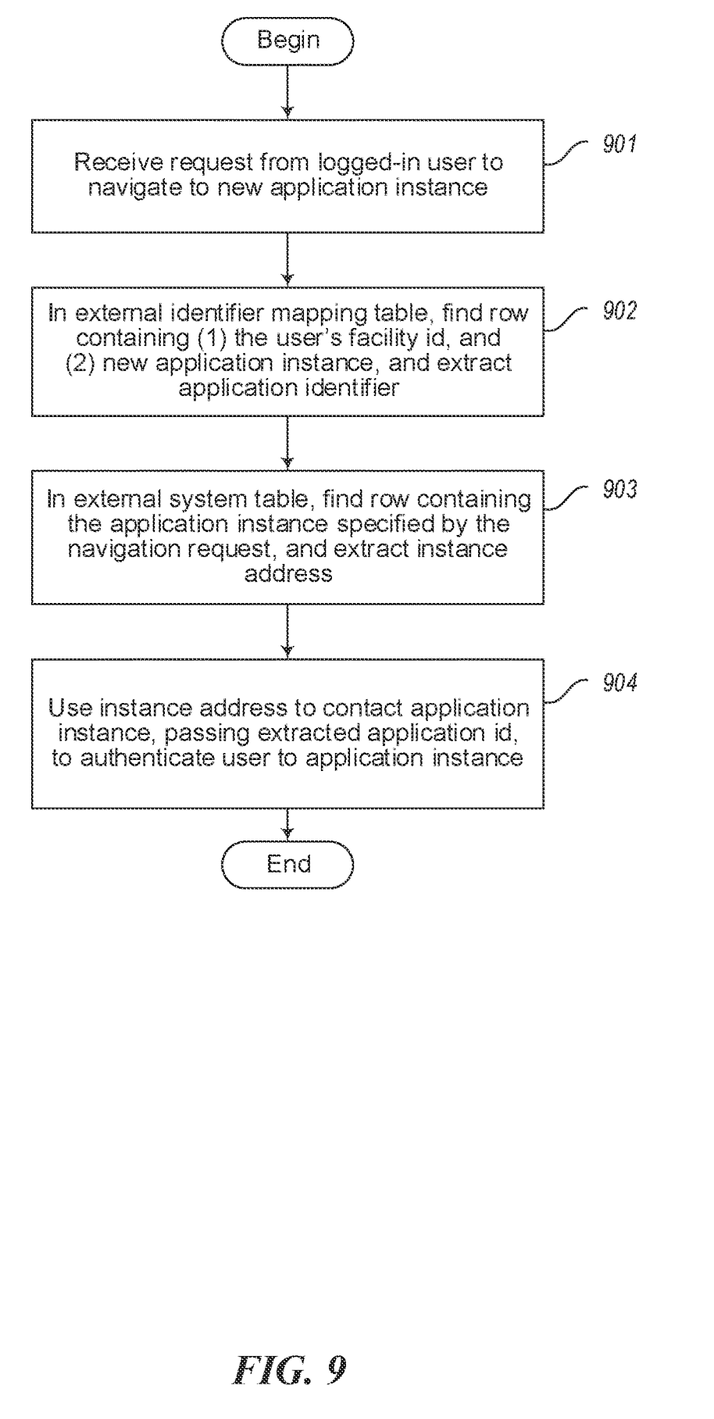
FIG. 9 is a flow diagram showing a process performed by the facility in some embodiments to switch among application instances for a user who is logged in to the facility.

FIG. 9 is a flow diagram showing a process performed by the facility in some embodiments to switch among application instances for a user who is logged in to the facility. In act 901, the facility receives a request from a user who is logged in to the facility to navigate to a new application instance for which they are registered. For example, a user named Bhuvanagiri Shivudu who has logged in to access the org.providence.epic.provorca Epic instance might request to switch to an org.providence.epic.provorak Epic instance in which he also has a record. In act 902, in the external identifier mapping table 600, the facility finds the row that contains the user's facility ID (determined in authenticating the user to the facility) and the application instance specified by the navigation request, and extracts from that row the external identifier value by which the application instance specified by the navigation request identifies the user. In the example, the facility finds row 612 containing the user's facility ID "a8dc" and application instance org.providence.epic.provorak, and extracts the application identifier "bshividu". In act 903, in the external system table 700, the facility finds the row containing the application instance specified by the navigation request, and extracts from this row the instance address for contacting the application instance specified by the navigation request. In the example, this is row 704. In act 904, the facility uses the extracted instance address to contact the application instance specified by the navigation request, passing to the application the application identifier extracted in act 902, to authenticate the user to this application instance. After act 904, this process concludes.

Figure 10:
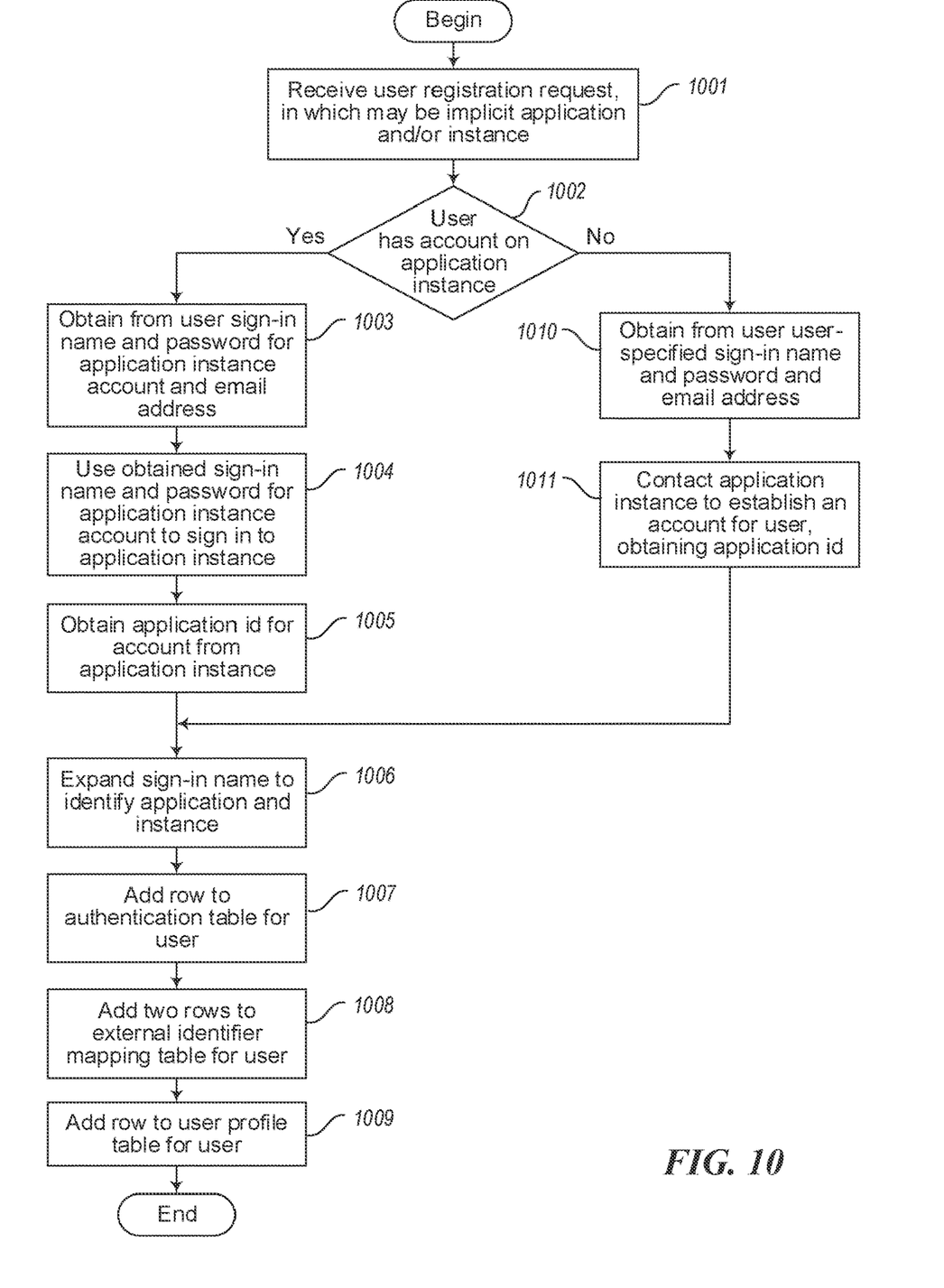
FIG. 10 is a flow diagram showing a process performed by the facility in some embodiments to register a new user with the facility.

FIG. 10 is a flow diagram showing a process performed by the facility in some embodiments to register a new user with the facility. In act 1001, the facility receives a user registration request, in which may be implicit an application and/or application instance which the user is already registered. In act 1002, if the user has an account on the application instance, then the facility continues in act 1003, else the facility continues in act 1010. In act 1003, the facility obtains from the user the sign-in name and password that the user uses with the application instance, and an email address. In act 1004, the facility uses the sign-in name and password for the application instance obtained in act 1003 to sign-in to the application instance on the user's behalf. In act 1005, the facility uses the sign-in to the application instance to obtain from the application instance the application ID for this account. In act 1006, the facility expands the sign-in name obtained in act 1005 to identify the application and instance. In act 1007, the facility adds a row to the authentication table for the user containing a new authentication ID generated for the user, as well as the expanded sign in name generated in act 1006 and the password obtained in act 1004. In act 1008, the facility adds two rows to the external identifier mapping table for the user: a first row mapping from the new authentication ID generated for the user to a new facility ID generated for the user, and a second row mapping from the new facility ID generated for the user to the application ID obtained in act 1005. In act 1009, the facility adds a row to the user profile table for the user. After act 1009, this process concludes.

In act 1010, the facility obtains from the user a user-specified sign-in name, password, and email address. In act 1011, the facility contacts the application instance to establish an account for the user, obtaining an application ID assigned by the application instance to identify the user. After act 1011, the facility continues in act 1006 to complete the process of registering the user.

In some embodiments, the facility is extensible, in that it can add authentication systems, applications, and application instances over time.

Figure 11:
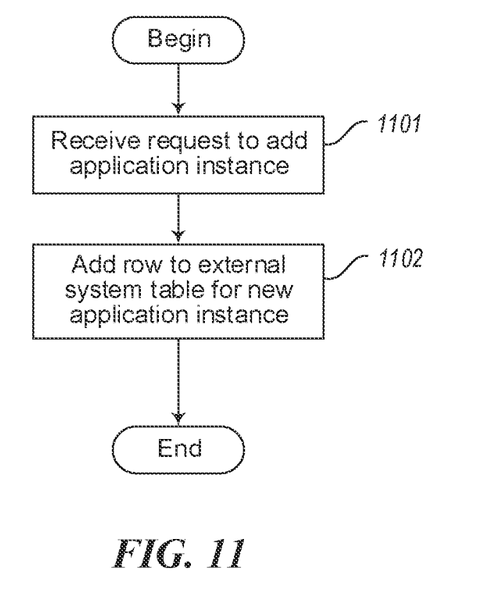
FIG. 11 is a flow diagram showing a process performed by the facility in some embodiments to add a new instance of an existing application.

FIG. 11 is a flow diagram showing a process performed by the facility in some embodiments to add a new instance of an existing application. In act 1101, the facility receives from an administrator a request to add an instance of an existing application. In act 1102, the facility adds a row to the external system table 500 for the new application instance, identifying the instance, the application, and the address at which it can be contacted. After act 1102, this process concludes.

Figure 12:
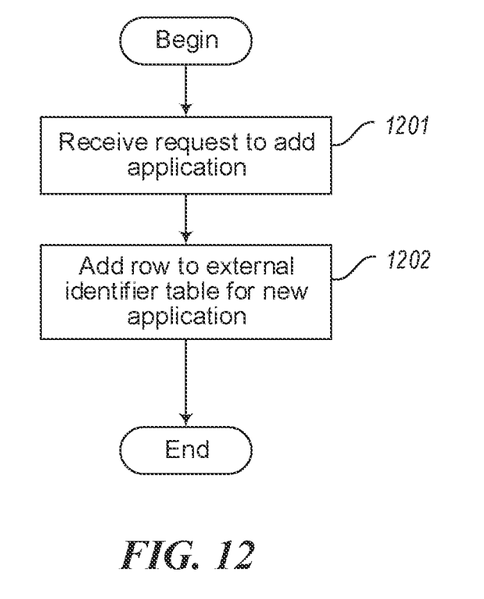
FIG. 12 is a flow diagram showing a process performed by the facility in some embodiments to add a new application.

FIG. 12 is a flow diagram showing a process performed by the facility in some embodiments to add a new application. In act 1201, the facility receives from an administrator a request to add an application. In act 1202, the facility adds a row to the external identifier table 700 for the new application that identifies the application and specifies the type of identifier the application uses to identify users. After act 1202, this process concludes.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method in a computing system, comprising:
for a user, at a first time, receiving an externally-created sign-in name and a password;
in response to the receiving at the first time:
expanding the received sign-in name to include text identifying an application instance;
hashing the received password to obtain a hash result; and
creating persistent state for the user comprising:
the expanded sign-in name;
a representation of the received password, the representation of the received password including the hash result; and
an identifier by which the user is known to the application instance;
at a second time later than the first time, receiving from the user the externally-created sign-in name and the password;
verifying the user by:
expanding the sign-in name received at the second time to include text identifying an application instance;
hashing the password received at the second time to obtain a hash result; and
verifying that the expanded sign-in name and hash password match the persistent state created for the user; and
in response to the verifying, using the identifier by which the user is known to the application instance to authenticate the user to the application instance.

2. The method of claim 1 wherein the received sign-in name was created by the application instance.

3. The method of claim 2 wherein the application instance is an instance of an electronic medical record application.

4. The method of claim 1 wherein the received sign-in name was created by the user.

5. The method of claim 1 wherein multiple persistent states are created to correspond to the same externally-created sign-in name, each with an expanded sign-in name identifying a different application instance, the method further comprising:
at a second time later than the first time, receiving from the user the externally-created sign-in name and the password;
hashing the password received at the second time to obtain a second hash result;
selecting one of the multiple persistent states whose password hash result matches the second hash result;
using the identifier by which the user is known to the application instance to authenticate the user to the application instance.

6. A method in a computing system, comprising:
for a user, at a first time, receiving an externally-created sign-in name and a password;
in response to the receiving at the first time:
expanding the received sign-in name to include text identifying an application instance; and
creating persistent state for the user comprising:
the expanded sign-in name;
a representation of the received password; and
an identifier by which the user is known to the application instance;
at a second time later than the first time, receiving from the user the externally-created sign-in name and the password;
determining that multiple persistent states were created to correspond to the same externally-created sign-in name, each with an expanded sign-in name identifying a different application instance;
at a third time later than the first time, obtaining demographic information from the user;
selecting one of the multiple persistent states having demographic information corresponding to the demographic information obtained from the user; and
using the identifier by which the user is known to the application instance to authenticate the user to the application instance.

7. A method in a computing system, comprising:
for a user, at a first time, receiving an externally-created sign-in name and a password;
in response to the receiving at the first time:
expanding the received sign-in name to include text identifying an application instance; and
creating persistent state for the user comprising:
the expanded sign-in name;
a representation of the received password; and
an identifier by which the user is known to the application instance;
at a second time later than the first time, receiving from the user the externally-created sign-in name and the password;
determining that multiple persistent states were created to correspond to the same externally-created sign-in name, each with an expanded sign-in name identifying a different application instance;
at a third time later than the first time, prompting the user to select an application instance;
expanding the sign-in name received at the second time to include text identifying the application instance selected by the user;
selecting one of the multiple persistent states having the expanded sign-in name received at the second time; and
using the identifier by which the user is known to the application instance to authenticate the user to the application instance.

8. One or more computer memory devices having contents configured to cause a computing system to perform a method, the method comprising:
receiving sign-in data from a distinguished user comprising a sign-in name and password;
generating a modified sign-in name by adding information identifying an application instance to the received sign-in name;
hashing the received password to obtain a first hash result; and
acting on behalf of the distinguished user based upon the generated modified sign-in name and the received password, wherein acting on behalf of the distinguished user comprises verifying the user by:
expanding a second sign-in name to include text identifying an application instance;
hashing a password to receive a second hash result;
verifying that the second sign-in name and second hash result match the modified sign-in name and first hash result; and
in response to the verifying, using the identifier by which the user is known to an application instance to authenticate the user to the application instance.

9. The one or more computer memories of claim 8 wherein the generating further adds information identifying an authenticating entity to the received sign-in name.

10. The one or more computer memories of claim 8 wherein the acting comprises:
logging the distinguished user in based upon the generated modified sign-in name and the received password; and
in response to logging the distinguished user in, automatically authenticating the distinguished user to the identified application instance.

11. The one or more computer memories of claim 8 wherein the acting comprises:
creating a persistent state usable for:
logging the distinguished user in based upon the generated modified sign-in name and the received password; and
in response to logging the distinguished user in, automatically authenticating the distinguished user to the identified application instance.

12. The one or more computer memories of claim 8 wherein the sign-in data further comprises an explicit indication of the application instance.

13. The one or more computer memories of claim 8 wherein the sign-in data is received in connection with a HTTP request having a referrer field,
the method further comprising discerning the identified application instance from contents of the referrer field.

14. The method of claim 6 wherein the received sign-in name was created by the application instance.

15. The method of claim 14 wherein the application instance is an instance of an electronic medical record application.

16. The method of claim 7 wherein the received sign-in name was created by the user.

\* \* \* \* \*